US00PP13730P29

(12) United States Plant Patent
Oudolf

(10) Patent No.: US PP13,730 P2
(45) Date of Patent: Apr. 22, 2003

(54) GEUM PLANT NAMED 'FLAMES OF PASSION'

(75) Inventor: Petrus Hendricus Oudolf, Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 10/139,958

(22) Filed: May 6, 2002

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A distinct cultivar of Geum plant named 'Flames of Passion', characterized by its upright plant habit; long flowering period; and red-colored flowers.

1 Drawing Sheet

BOTANICAL CLASSIFICATION/CULTIVAR DESIGNATION

*Geum rivale* cultivar 'Flames of Passion'.

BACKGROUND OF THE INVENTION

The present Invention relates to a new and distinct cultivar of Geum plant, botanically known as *Geum rivale,* and hereinafter referred to by the cultivar name Flames of Passion.

The new Geum originated from a chance cross-pollination of two unidentified selections of *Geum rivale,* not patented. The new Geum was discovered by the Inventor in 1999 in Hummelo, The Netherlands. Plants of the new Geum differed primarily from plants of the unidentified parental selections in flower orientation and flower color.

Asexual reproduction of the new cultivar by divisions in Hemmelo, The Netherlands since 1999, has shown that the unique features of this new Geum are stable and reproduced true to type in successive generations.

SUMMARY OF THE INVENTION

Plants of the cultivar Flames of Passion have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Flames of Passion'. These characteristics in combination distinguish 'Flames of Passion' as a new and distinct cultivar:

1. Upright plant habit.
2. Long flowering period.
3. Red-colored flowers.

Plants of the new Geum can be compared to plants of an unidentified selection of *Geum rivale,* not patented. In side-by-side comparisons conducted in Hummelo, The Netherlands, plants of the new Geum differed from of the unidentified selection of *Geum rivale* in the following characteristics:

1. Plants of the new Geum flowered for a longer period of time than plants of the unidentified selection of *Geum rivale.*

2. Flowers of plants of the new Geum were more upright than flowers of plants of the unidentified selection of *Geum rivale.*
3. Flowers of plants of the new Geum were darker red in color than flowers of plants of the unidentified selection of *Geum rivale.*

BRIEF DESCRIPTION OF THE PHOTOGRAPH

The accompanying colored photograph illustrates the overall appearance of the new Geum, showing the colors as true as it is reasonably possible to obtain in colored reproductions of this type. Colors in the photograph may differ slightly from the color values cited in the detailed botanical description which accurately describe the colors of the new Geum. The photograph comprises a side perspective view of a typical one-year old flowering plant of 'Flames of Passion' grown in a container.

DETAILED BOTANICAL DESCRIPTION

In the following description, color references are made to The Royal Horticultural Society Colour Chart, 2001 Edition, except where general terms of ordinary dictionary significance are used. Plants used for the following description were about one year old and grown under outdoor field conditions which closely approximate commercial production conditions during the spring and summer in Hummelo, The Netherlands.

Botanical classification: *Geum rivale* cultivar Flames of Passion.

Parentage: Cross-pollination of two unidentified selections of *Geum rivale,* not patented.

Propagation:

*Type.*—By divisions.

*Root description.*—Small, fine; freely branching.

Plant description:

*Form.*—Perennial flowering plant; upright plant habit; basal branching; moderately vigorous growth habit.

*Plant height.*—About 40 cm.

*Plant diameter.*—About 30 cm.

*Basal branch description.*—Number per plant: About two. Length: About 40 cm. Diameter: About 2 mm. Internode length: About 6 cm. Strength: Moderately strong. Texture: Pubescent. Color: N186C.

*Foliage description*.—Arrangement: Alternate, compound with typically three leaflets. Length, terminal leaflets: About 5 cm. Length, lateral leaflets: About 1.2 cm. Width, terminal leaflets: About 6 cm. Width, lateral leaflets: About 8 mm. Shape, terminal leaflets: Roughly rhomboidal. Shape, lateral leaflets: Ovate to elliptic. Apex, terminal and lateral leaflets: Acute. Base, terminal and lateral leaflets: Cuneate. Margin, terminal and lateral leaflets: Biserrate. Texture, terminal and lateral leaflets, upper and lower surfaces: Pubescent. Venation pattern, terminal and lateral leaflets: Palmate. Petiole: Length: About 9 cm. Diameter: About 2.5 mm. Texture: Pubescent. Color, terminal and lateral leaflets: Young foliage, upper surface: 138A to 143A. Young foliage, lower surface: 138B. Fully expanded foliage, upper surface: 137A to 137B. Fully expanded foliage, lower surface: 138B. Venation, upper surface: 137A to 137B. Venation, lower surface: 144A. Petiole: 143B to 143C.

Flower description:

*Appearance*.—Single rotate flowers with 18 petals arranged with one to four flowers per corymb. Flowers not persistent.

*Quantity of flowers*.—About six flowers per plant develop during the flowering season.

*Natural flowering season*.—End of May to early July in Hummelo, The Netherlands.

*Fragrance*.—None detected.

*Flower longevity*.—About one to two weeks.

*Inflorescence height*.—About 40 cm.

*Inflorescence diameter*.—About 10 cm.

*Flower diameter*.—About 2.8 cm.

*Flower depth* (*height*).—About 1.4 cm.

*Flower buds*.—Length: About 1 cm. Diameter: About 1.2 cm. Shape: Ovoid. Color: N186C to 187A.

*Petals*.—Quantity per flower: About 18. Arrangement: Rotate, overlapping. Length: About 1 cm. Width: About 1.2 cm. Shape: Flabellate to spatulate. Apex: Retuse. Base: Attenuate. Margin: Entire. Texture, upper and lower surface: Smooth, glabrous. Color: When opening, upper surface: N34C to 39A. When opening, lower surface: 39A. Fully opened, upper and lower surfaces: 45C, becoming closer to 47A to 47B with subsequent development.

*Sepals*.—Quantity per flower: About ten. Arrangement: Rotate. Calyx length: About 3 mm. Calyx diameter: About 2.4 cm. Sepal shape: Linear to lanceolate. Sepal apex: Acute. Sepal margin: Entire. Sepal texture, upper and lower surfaces: Pubescent. Color, upper surface: 177B to 187B. Color, lower surface: 187A.

*Peduncles*.—Length: About 40 cm. Diameter: About 2 mm. Angle: Erect to about 45° from vertical. Strength: Moderately strong. Color: N186C.

*Pedicels*.—Length: About 10 cm. Diameter: About 1.5 mm. Angle: Erect to about 35° from vertical. Strength: Moderately strong. Color: N186C.

*Reproductive organs*.—Stamens: Quantity per flower: More than 50. Anther shape: Reniform; dorsifixed. Anther length: About 1 mm. Anther diameter: Less than 0.4 mm. Anther color: Close to 7A. Pollen amount: Scarce. Pollen color: Close to 7A. Pistils: Quantity per flower: About 40. Pistil length: About 6 mm. Style length: About 6 mm. Style color: 182A. Stigma color: Light grayed purple. Ovary color: 143C.

*Fruit*.—Quantity per plant: About 200. Type: Achene. Length: About 1 cm. Diameter: About 1 mm. Color: N186C to 187A.

*Seed*.—Length: About 2 mm. Diameter: About 1 mm. Color: Close to 200C.

Disease/pest resistance: Plants of the new Geum have not been noted to be resistant to pathogens or pests common to Geum.

Temperature tolerance: Plants of the new Geum are tolerant to temperatures from about −20 to 35° C.

It is claimed:

1. A new and distinct cultivar of Geum plant named 'Flames of Passion', as illustrated and described.

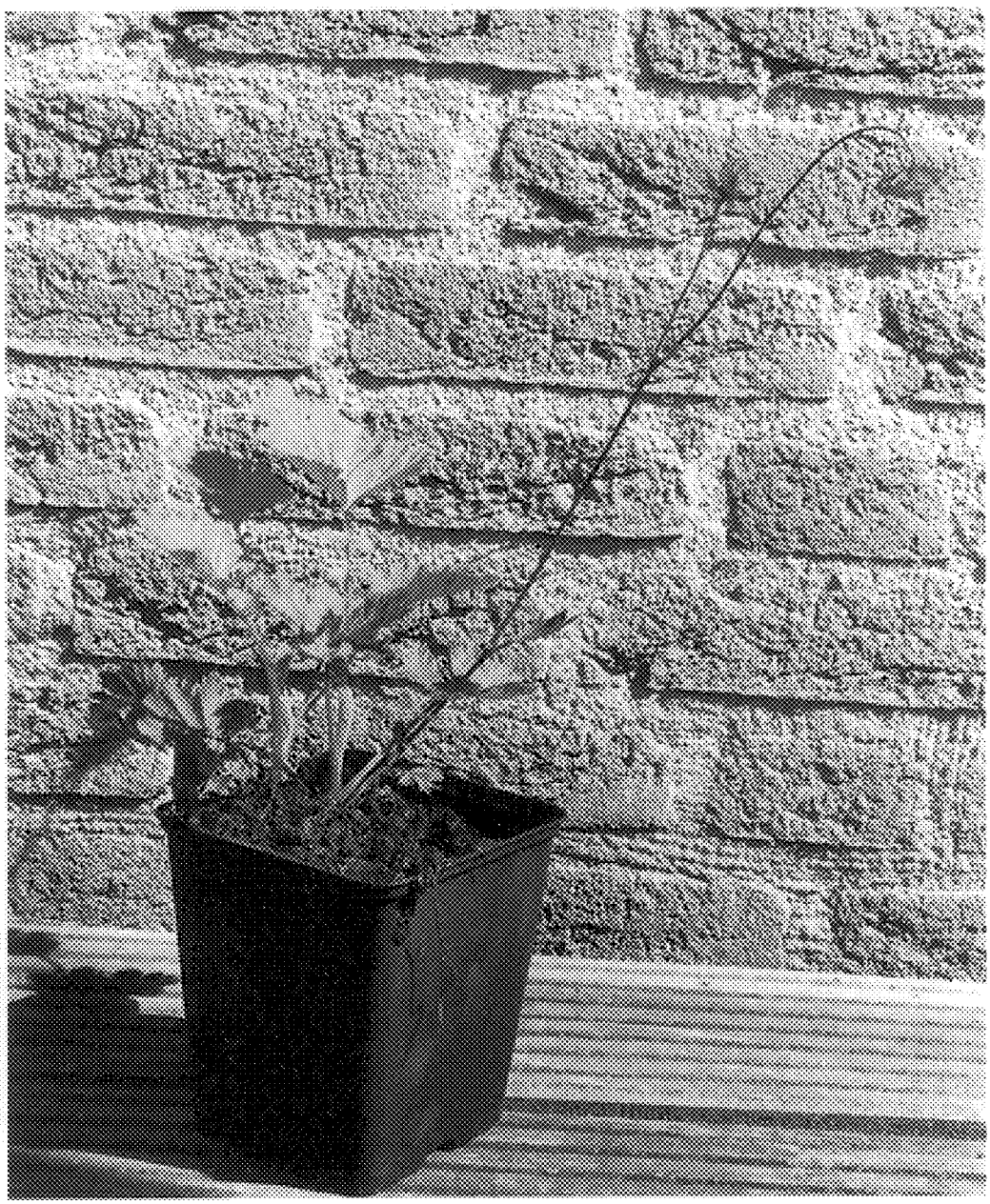

* * * * *